(12) United States Patent
Stauffer

(10) Patent No.: US 7,253,328 B2
(45) Date of Patent: Aug. 7, 2007

(54) METHOD FOR PRODUCING VINYL CHLORIDE MONOMER

(76) Inventor: John Stauffer, 6 Pecksland Rd., Greenwich, CT (US) 06831

( * ) Notice: Subject to any disclaimer, the term of this patent is extended or adjusted under 35 U.S.C. 154(b) by 201 days.

(21) Appl. No.: 11/039,903

(22) Filed: Jan. 24, 2005

(65) Prior Publication Data
US 2006/0167325 A1   Jul. 27, 2006

(51) Int. Cl.
C07C 17/26 (2006.01)
(52) U.S. Cl. .................................... 570/237
(58) Field of Classification Search ............... 570/216, 570/257, 224, 226, 230, 238
See application file for complete search history.

(56) References Cited

U.S. PATENT DOCUMENTS

2005/0027084 A1 * 2/2005 Clarke et al. ............... 526/68
2005/0124835 A1 * 6/2005 Benje et al. ................ 570/220

FOREIGN PATENT DOCUMENTS

JP        05262682    *  8/1993

* cited by examiner

Primary Examiner—Karl Puttlitz
(74) Attorney, Agent, or Firm—Patton Boggs LLP

(57) ABSTRACT

A method is provided for producing vinyl chloride monomer from methyl chloride and methylene chloride. In the method, methyl chloride is reacted with methylene chloride in the vapor phase in the presence of a catalyst to produce vinyl chloride and hydrogen chloride. The reaction temperature is in the range of from about 300° C. to 500° C. The catalyst is selected from the group alumina gel, gamma-alumina, zinc chloride on active alumina, silica-alumina, zeolite, and silicon-aluminum-phosphorus oxide.

11 Claims, 1 Drawing Sheet

METHOD FOR PRODUCING VINYL CHLORIDE MONOMER

FIELD OF THE INVENTION

The present invention relates to a method for producing vinyl chloride monomer (VCM) from methyl chloride and methylene chloride. The two reactants are combined in the vapor phase in the presence of a catalyst to produce VCM and a byproduct, hydrogen chloride.

BACKGROUND OF THE INVENTION

Historically two industrial processes have been used for the production of vinyl chloride monomer. A good overview of this activity is given in Kirk-Othmer, *Encyclopedia of Chemical Technology*, 4$^{th}$ ed., Vol. 24, pp. 872–875. The first general method for the preparation of VCM involved the addition of hydrogen chloride to acetylene to give vinyl chloride directly. Newer processes that rely on ethylene as a raw material have now largely supplanted this process. Using one of several methods, ethylene is converted to ethylene dichloride (EDC), which is thermally cracked to produce VCM and byproduct hydrogen chloride. By recycling the hydrogen chloride, balanced processes are achieved.

Because ethylene comprises about 45 weight percent of VCM, the cost of ethylene is a major factor in the manufacturing cost. As a result, there exists an interest to find a less expensive hydrocarbon raw material. The most likely candidates are ethane and methane, but so far, attempts have been frustrated by the relative inactivity of these two hydrocarbons.

Therefore, it is an object of the present invention to substitute a cheaper source of hydrocarbon for ethylene in the manufacture of VCM. Another object is to provide a method that gives high yields of product. These and other objects, features and advantages will be apparent from the following description.

SUMMARY OF THE INVENTION

A method is provided for producing vinyl chloride from methyl chloride and methylene chloride. The two starting materials are reacted together in the vapor phase in the presence of a catalyst to give vinyl chloride and hydrogen chloride. The temperature of the reaction is in the range of from about 300° C. to about 500° C. The pressure may vary from about 1 atmosphere to about 10 atmospheres.

The catalyst is selected from the group comprising alumina gel, gamma-alumina, zinc chloride on active alumina, silica-alumina, zeolite, and silicon-aluminum-phosphorus oxide.

DETAILED DESCRIPTION OF THE PROCESS

Figure 1:
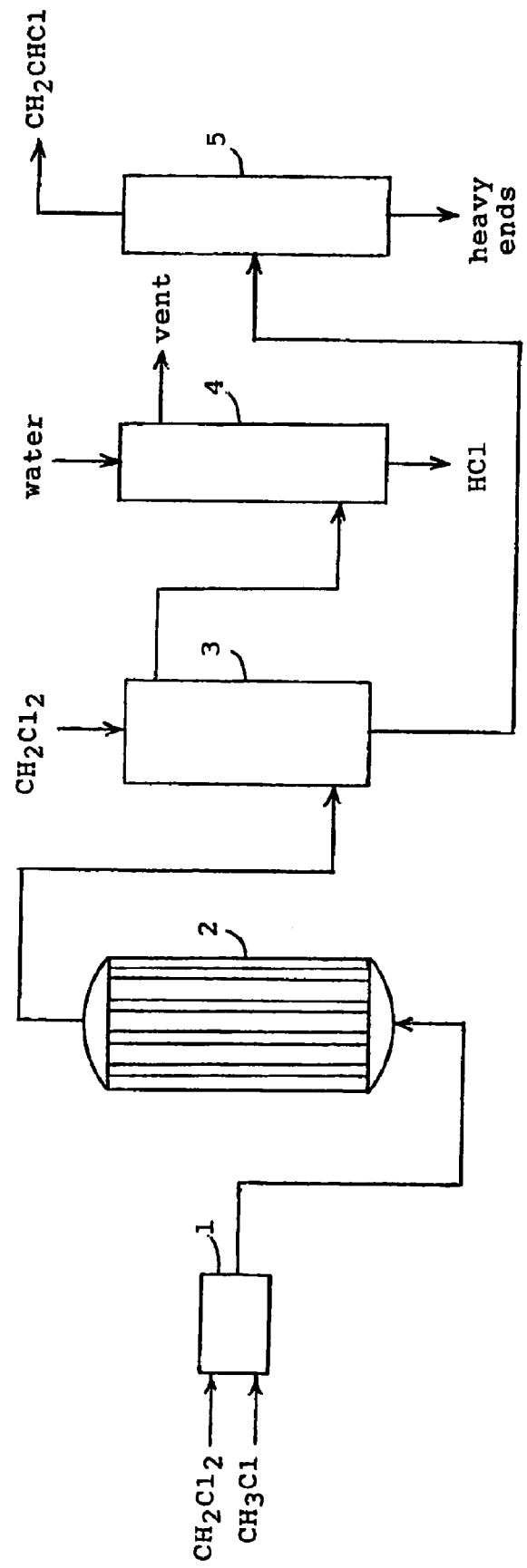
FIG. 1 illustrates a process block flow diagram of the present method for producing vinyl chloride monomer.

In the process of the present invention, one molecule of methyl chloride ($CH_3Cl$) is reacted with one molecule of methylene chloride ($CH_2Cl_2$) in the presence of a catalyst to produce one molecule of vinyl chloride ($CH_2CHCl$) and two molecules of hydrogen chloride (HCl). The reaction can be represented by the following equation.

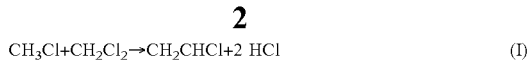

$$CH_3Cl + CH_2Cl_2 \rightarrow CH_2CHCl + 2\,HCl \qquad (I)$$

The thermodynamics for this reaction is highly favorable so that the reaction essentially goes to completion. Using data for the enthalpies and the Gibbs energies of formation for the reactants and the products, the equilibrium constant was determined for several reaction temperatures. Thus, the logarithm of the equilibrium constant $K_p$ equals 4.59 at 300° C., 5.00 at 400° C., and 5.32 at 500° C. The thermodynamic data also indicate that the reaction is endothermic so that heat must be supplied to the reaction.

The results for the conversions at the given temperatures would suggest that the reaction could be carried out favorably at elevated temperatures without the need for a catalyst. This assumption would be correct except for the fact that byproducts most likely would also be formed along with the desired vinyl chloride product. For example, methylene chloride could react with itself to form 1,2-dichloroethylene (CHClCHCl) a compound for which there is little demand.

In order to promote the selectivity of the process, the reaction is carried out in the presence of a catalyst that favors the formation of vinyl chloride. By postulating the reaction mechanism, effective catalysts for the reaction were determined. These catalysts are widely used in chemical synthesis and are therefore readily available.

The reaction mechanism which best fits the parameters of the process can be represented by the following equations.

$$CH_3Cl + H_2O \rightarrow CH_3OH + HCl \qquad (II)$$

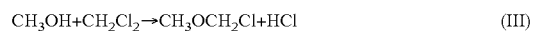
$$CH_3OH + CH_2Cl_2 \rightarrow CH_3OCH_2Cl + HCl \qquad (III)$$

$$CH_3OCH_2Cl \rightarrow CH_2CHCl + H_2O \qquad (IV)$$

When equations (II), (III), and (IV) are combined, the result is identical to equation (I).

Though the process is carried out under generally anhydrous conditions, the catalytic amount of water required by the reaction in equation (II) is continually produced by the reaction products in equation (IV) and also from a a catalytic amount water that is preferably chemisorbed on the catalyst surface.

The reaction shown by equation (II) is the reverse of methanol hydrochlorination, which is a well-known industrial process. (Kirk-Other, *Encyclopedia of Chemical Technology* 4$^{th}$ ed., volume 5, page 1034, John Wiley & Co.). This reaction is catalyzed by numerous catalysts including alumina gel, gamma-alumina, zinc chloride on active alumina, silica-alumina, zeolites, and silicon-aluminum-phosphorus oxide. These catalysts are preferably effective in the temperature range from about 295° C., to about 350° C. Although equilibrium conditions favor the formation of methyl chloride and water from methanol and hydrogen chloride, reaction II will proceed inasmuch as methanol is continuously removed by reaction III. The reaction given by equation (III) is between an alcohol and an alkyl halide. Such a reaction has been reported in the literature as a means of preparing ethers. (*Chemical & Engineering News*, Feb. 15, 1999, page 51). The reaction is self-catalyzed and takes place with mild heating. The conditions for reaction III can be surmised from the conditions for the reaction of methyl alcohol with methyl chloride to form dimethyl ether and hydrogen chloride. Thermodynamics for this latter reaction shows that the logarithm of the equilibrium constant at 25° C. is −2.24. Because the reaction is endothermic the equilibrium constant is more favorable at higher temperatures. In any case, reaction III is driven to the right by the removal of chloromethyl methyl ether in reaction IV.

Finally, the reaction of equation (IV) is similar to the formation of ethylene from dimethyl ether. This latter reaction has been studied extensively as a means of producing olefins from methyl alcohol. (*Chemical Engineering*, January 1996, page 17). In one aspect of the present invention, the reaction of equation (IV) is catalyzed by a zeolite-type catalyst of silicon-aluminum-phosphorus oxide at a temperature in the range of 350° C. to 500° C. at a pressure of from about 1 bar to about 5 bars. In another aspect of the present invention, the reaction is also catalyzed by the zeolite ZSM-5 that comprises silica-alumina. (J. H. Gregor, 1996 *World Methanol Conference*, Chemical Market Associates, Inc., Houston, Tex., pages 187–188). Additionally, zinc chloride is known to activate the carbon-oxygen bond in ethers, making possible the reaction of these compounds. (*J. Am. Chem. Soc.*, 46, 753 (1924)).

In view of the aforementioned data, the reaction of the present invention is preferably promoted by a catalyst comprising alumina gel, gamma-alumina, zinc chloride, silica-alumina, zeolites, or silicon-aluminum-phosphorus oxide. It is known that in many reactions, the results with silica-alumina catalysts are similar to those with alumina. The operating temperature for the reaction is in the range of about 300° C. to about 500° C., and the pressure is in the range of about 1 atmosphere to about 10 atmospheres.

A schematic flow diagram of an embodiment of the method is shown in FIG. 1. Methyl chloride gas and methylene chloride vapor are fed to static mixer 1 and then to reactor 2, which preferably comprises tubes packed with catalyst. In this embodiment, the tubes are directly heated in a furnace, such as those commonly found in chemical processes. The effluent gases from the reactor are cooled in quench tower 3 by a stream of methylene chloride, which absorbs the vinyl chloride and heavy ends. The non-condensed gases are fed to stripper column 4 in which the hydrogen chloride is removed before the gases are vented. The liquid stream from the quench tower is pumped to distillation column 5 that separates the vinyl chloride product from the heavy ends. The fractionation of vinyl chloride from the quench stream is facilitated by the fact that vinyl chloride has a boiling point of –13.9° C. whereas methylene chloride boils at +40.2C.

Vinyl chloride from the present invention meets the specifications for monomer used in large quantities by the plastics industry. In view of the advantages of the present invention over the prior art, the disclosed method has great utility.

What is claimed:

1. A method for producing vinyl chloride comprising the reaction of methyl chloride with methylene chloride in the vapor phase in the presence of a catalyst selected from the group consisting of alumina gel, gamma-alumina, zinc chloride on active alumina, silica-alumina, zeolite, and silicon-aluminum-phosphorus oxide to produce said vinyl chloride and a byproduct of hydrogen chloride, wherein the molar ratio of said methyl chloride and said methylene chloride is 1 to 1.

2. The method according to claim 1 wherein said reaction is conducted at a temperature in the range of from about 300° C. to about 500° C.

3. The method according to claim 1 wherein said reaction is conducted at a pressure m the range of from about 1 atmosphere to about 10 atmospheres.

4. The method according to claim 1 wherein said catalyst contains water.

5. A method for producing vinyl chloride monomer, comprising:
   reacting methyl chloride and methylene chloride in the presence of a catalyst to produce a reactor effluent;
   quenching said reactor effluent to produce a vapor stream and a liquid stream; and
   separating said liquid stream into a vinyl chloride monomer stream and a heavy ends stream.

6. The method for producing vinyl chloride monomer of claim 5 wherein said catalyst is selected from the group consisting of alumina gel, gamma-alumina, zinc chloride on active alumina, silica-alumina, zeolite, and silicon-aluminum-phosphorus oxide.

7. The method for producing vinyl chloride monomer of claim 5 wherein said reaction is conducted at a temperature in the range of from about 300° C. to about 500° C.

8. The method for producing vinyl chloride monomer of claim 5 wherein said reaction is conducted at a pressure in the range of from about 1 atmosphere to about 10 atmospheres.

9. The method for producing vinyl chloride monomer of claim 5, further comprising
   recycling said vapor stream to catalytically react with said methyl chloride and said methylene chloride in said reacting step.

10. The method for producing vinyl chloride monomer of claim 5 wherein the molar ratio of said methyl chloride and said methylene chloride is 1 to 1.

11. The method for producing vinyl chloride monomer of claim 5 wherein said catalyst includes an effective amount of water for said reacting step.

* * * * *